United States Patent [19]

Matsushita et al.

[11] Patent Number: 4,832,049
[45] Date of Patent: May 23, 1989

[54] APPARATUS FOR DETECTING ABNORMALITY OF THE SPINAL COLUMN

[75] Inventors: Machiko Matsushita, Yokohama; Masahiro Watabe, Funabashi, both of Japan

[73] Assignee: Canon Kabushiki Kaisha, Tokyo, Japan

[21] Appl. No.: 120,686

[22] Filed: Nov. 9, 1987

Related U.S. Application Data

[63] Continuation of Ser. No. 725,625, Apr. 22, 1985, abandoned.

[51] Int. Cl.$^4$ .............................................. A61B 5/10
[52] U.S. Cl. ....................................... 128/781; 128/665; 33/512; 358/107
[58] Field of Search ............... 128/653, 665, 781, 782, 128/774; 33/511, 512; 356/2; 358/107

[56] References Cited

U.S. PATENT DOCUMENTS

| | | | |
|---|---|---|---|
| 3,218,389 | 11/1965 | Reed | 358/107 |
| 3,533,684 | 10/1970 | Stark et al. | 358/107 X |
| 3,551,052 | 12/1970 | Reiber | 358/107 X |
| 4,600,012 | 7/1986 | Kohayakawa et al. | 128/781 |

FOREIGN PATENT DOCUMENTS 1211962  3/1960  France .................. 128/781

Primary Examiner—Kyle L. Howell
Assistant Examiner—John C. Hanley
Attorney, Agent, or Firm—Fitzpatrick, Cella, Harper & Scinto

[57] ABSTRACT

An apparatus for detecting an abnormality of the spinal column is provided with apparatus for obliquely applying at least one light beam to each of the left and right backs of a subject in parallel with an imaginary spinal line, and apparatus for comparing and detecting the positions on the left and right backs to which the light beams have been applied.

20 Claims, 7 Drawing Sheets

APPARATUS FOR DETECTING ABNORMALITY OF THE SPINAL COLUMN

This application is a continuation of application Ser. No. 725,625 filed Apr. 22, 1985, now abandoned.

BACKGROUND OF THE INVENTION

1. Field of the Invention

This invention relates to an apparatus for detecting an abnormality of the spinal column.

2. Description of the Prior Art

A disease in which the spinal column bends to the left or right, as is often found in children (scoliosis), has heretofore posed problems.

As a method for detecting such disease, the Moire method of forming Moire stripes on the entire back of the subject and judging whether the distribution of the Moire stripes is balanced on the left and right sides of the back with respect to the spinal column has been adopted, but this method suffers from a disadvantage that when judging, the examiner becomes fatigued with the Moire stripes and analysis of data is not easy. As another detecting method, there is a method of x-ray-photographing the spinal column and directly judging the abnormality thereof, but this method leaves the problem of exposure to x-rays and is usually used only in precise medical examinations.

SUMMARY OF THE INVENTION

It is an object of the present invention to provide an apparatus which can simply detect the unbalance of the protuberances of the left and right backs based on the curvature of the spinal column.

It is a further object of the present invention to provide an apparatus which can accomplish the screening of an abnormality of the spinal column which replaces the visual diagnosis, simultaneously with the measurement of the stature of the subject.

DESCRIPTION OF THE PREFERRED EMBODIMENTS

Figure 1:
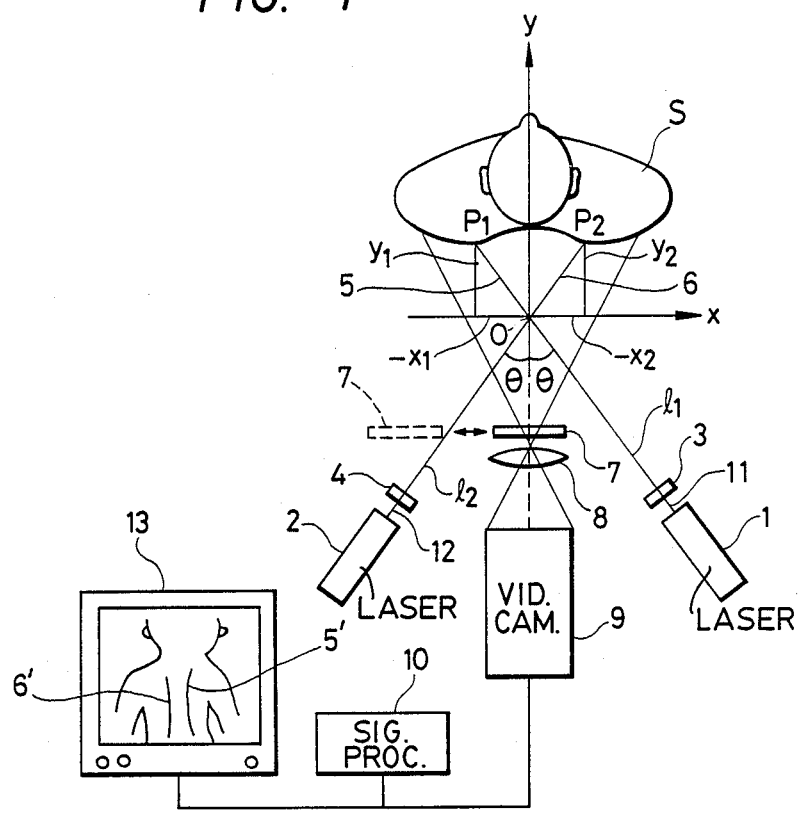
FIG. 1 shows an embodiment of the apparatus according to the present invention.

FIG. 1 shows a first embodiment of the apparatus according to the present invention. A beam 11 emitted from a laser 1 is widened in a direction perpendicular to the plane of the drawing sheet by a cylindrical lens 3 whose generatrix direction is in the plane of the drawing sheet, and is obliquely applied to the left back of a subject S at an angle of application $\theta$. On the other hand, a beam 12 emitted from a laser 2 is widened in a direction perpendicular to the plane of the drawing sheet by a cylindrical lens 4 whose generatrix direction is in the plane of the drawing sheet, and is obliquely applied to the right back of the subject S at an angle of application $\theta$.

Slit beams 5 and 6 applied to the left and right sides with respect to the spinal column of the subject S are caught by a video camera 9 through a lens 8 and are imaged as 5' and 6' on a monitor 13, and the video signals from the video camera 9 are processed by a signal processor 10.

It is known that the uneven state of the back becomes bilaterally asymmetrical if the subject has any abnormality of the spinal column, such as scoliosis, and the present invention uses this information. That is, when, with the point at which a beam $l_1$ emitted from the laser 1 in FIG. 1 and a beam $l_2$ emitted from the laser 2 intersect each other as the reference point, the coordinates of a position $P_1$ at which the beam $l_1$ is applied to the back are $x_1$, $y_1$, and the coordinates of a position $P_2$ at which the beam $l_2$ is applied to the back are $x_2$, $y_2$, the following equations are established:

$$y_1 = -x_1/\tan \theta$$

$$y_2 = x_2/\tan \theta$$

The abnormality of the spinal column can be judged by detecting the interval difference $|x_1| - |x_2|$ between the light beam application position and the imaginary spinal line along the direction of the imaginary spinal line which is the center line of the subject body, i.e., the direction perpendicular to x direction and y direction, but clinically it is desirable to detect the value of $\Delta y = y_1 - y_2$ along the direction of the imaginary spinal line and judge whether it is within the permissible range.

If a single beam is applied to the back, the bending in the front-to-back direction (the depth direction) of the spinal column can be recognized but whether it is scoliosis cannot be judged, whereas in the present invention, a beam is obliquely applied to each of the left side and the right side of the back, whereby an abnormality of the spinal column can be judged from the asymmetry of the unevenness of the left and right backs peculiar to the abnormality of the spinal column such as scoliosis. The setting of the imaginary spinal line can be accomplished by one of various conventional means.

In FIG. 1, reference numeral 7 designates a filter which transmits therethrough only the wavelength of the applied laser light. The filter 7 is removably inserted in the optical path.

Figure 2:
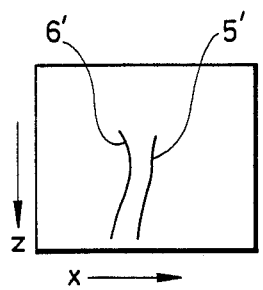
FIG. 2 shows the image when a wavelength selecting filter is inserted in the optical path.

FIG. 2 shows the image when the filter 7 which transmits therethrough only the wavelength of the applied laser light is inserted into the optical path. Only the applied beam can be clearly detected by the filter 7.

Figure 3:
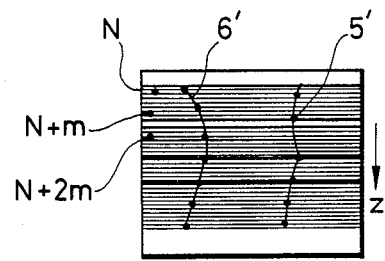
FIG. 3 shows the left and right light application positions on scanning lines spaced apart from one another by an arbitrary distance.
Figure 4:
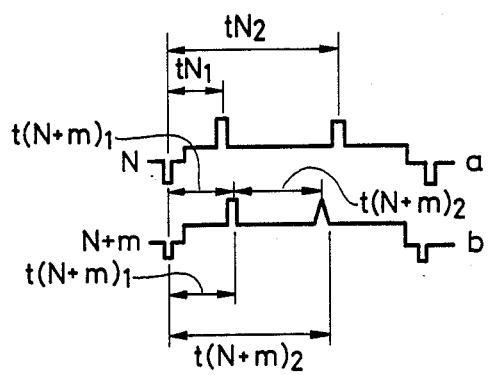
FIG. 4 shows the Nth and (N+m)th video signals.

FIG. 3 shows the left and right light application positions on the Nth, (N+m)th, (N+2m)th, . . . scanning lines, and FIG. 4 shows video signals.

In FIG. 4, a letter a designates the Nth video signal and a letter b denotes the (N+m)th video signal. The times $t_{N1}$ and $t_{(N+m)1}$ from the respective horizontal synchronizing signals to the position to which the left side light beam is applied and the times $t_{N2}$ and $t_{(N+m)2}$ from the respective horizontal synchronizing signal to the position to which the right side light beam is applied are measured and abnormality is detected from the distribution of the two interval differences.

When detecting the signals, there are obtained high level signals at 5' and 6' and therefore, a suitable threshold can be easily set. The filter 7 is useful in processing the signals and eliminating any noise.

Figure 5:
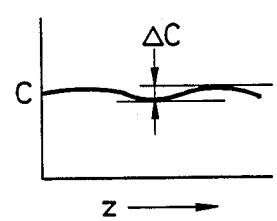
FIGS. 5 and 6 show the distributions of the interval differences when abnormality of the spinal column is absent and when abnormality of the spinal column is present, respectively.
Figure 6:
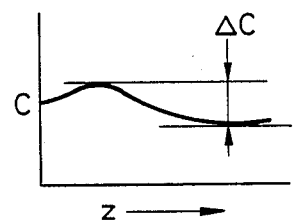

FIGS. 5 and 6 show the distribution of the interval difference C between the left and right light application positions and the imaginary spinal line in the direction of imaginary spinal line (Z direction).

As shown in FIG. 5, the interval difference C is within the permissible range if there is no abnormality of the spinal column, but as shown in FIG. 6, the interval difference C exceeds the permissible range and can be thereby discriminated if there is an abnormality of the spinal column.

Figure 7:
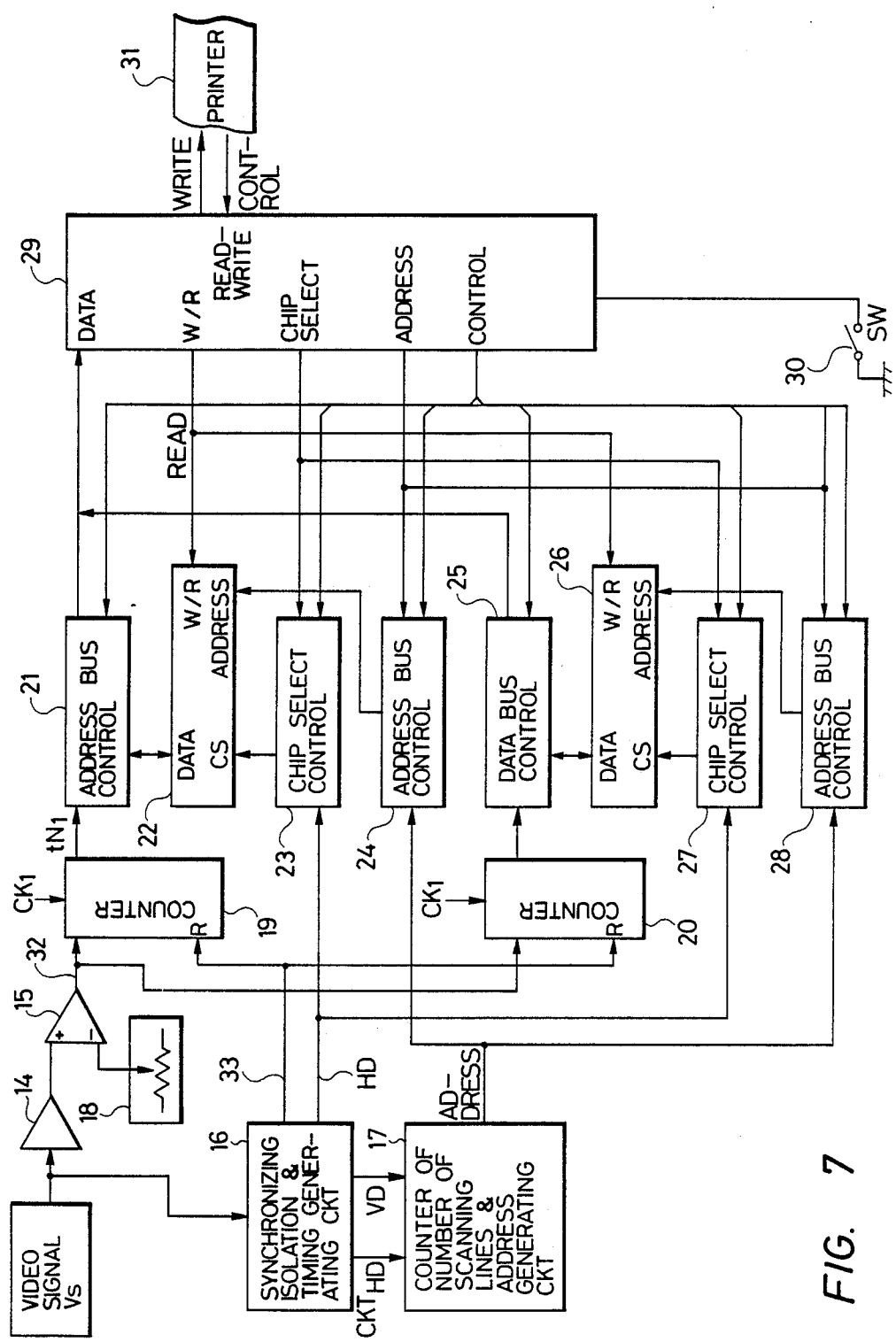
FIG. 7 is a block diagram of a signal processor.

FIG. 7 shows a block diagram of the signal processor 10 of FIG. 1.

A video signal Vs enters an image amplifier 14 and a level higher than the threshold set by a voltage setter 18 is binarized as Hi output by a binarizing comparator 15.

Reference numeral 19 designates a counter for counting the clock number of the time $t_{N1}$ from a horizontal synchronizing signal $H_D$ to the left side beam application position. The output of the counter 19 is input to a data bus control circuit 21. The data bus control circuit 21 functions as a switch for selecting the inputs to a memory 22 and CPU 29.

On the other hand, reference numeral 20 denotes a counter for counting the clock number of the time $t_{N2}$ from the horizontal synchronizing signal $H_D$ to the right side beam application position. The output of the counter 20 is input to a data bus control circuit 25.

Figure 8:
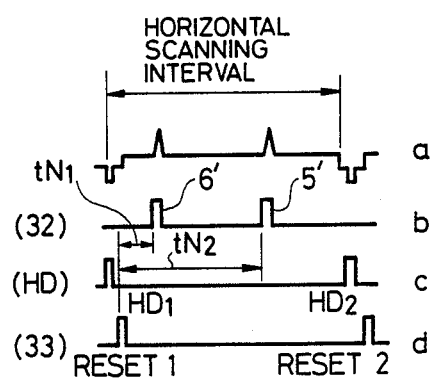
FIGS. 8 and 9 illustrate timing signals perceived in horizontal and vertical scanning intervals, respectively.

The two counters 19 and 20 are reset at the timing of the reset 1 of FIG. 8d and count $t_{N1}$ and $t_{N2}$, respectively, and cause memories 22 and 26 to read the contents thereof at $H_{D2}$ through the data bus control circuits 21 and 25. It is to be understood that this operation is effected for each scanning line.

The addresses in the memories from address bus control circuits 24 and 28 the address signals as shown in FIGS. 9e–9h produced by a counter of number of scanning lines and address generating circuit 17.

Figure 9:
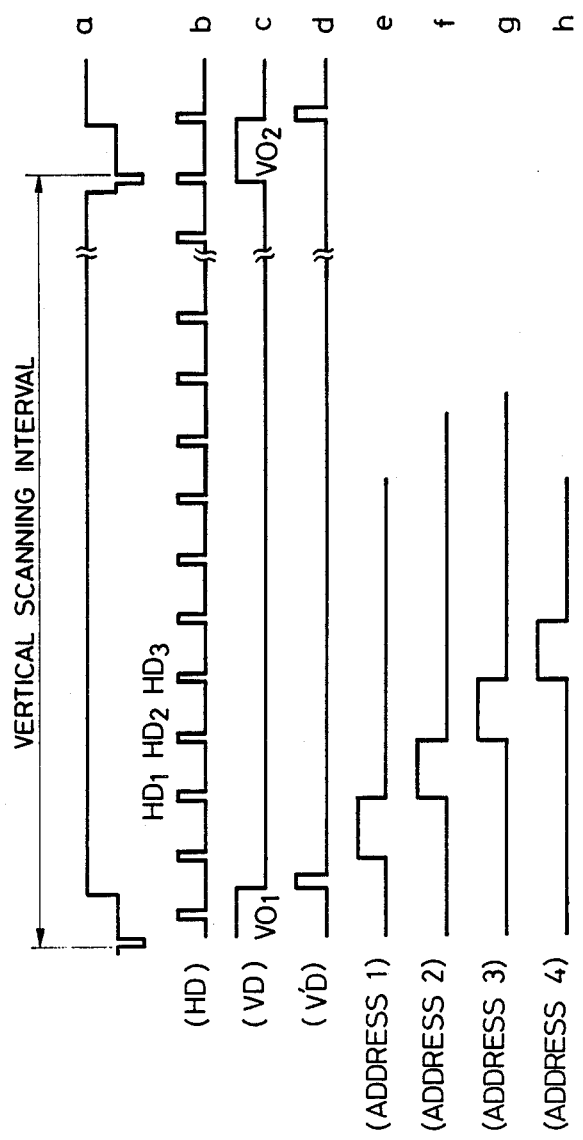

The CPU 29 is normally not related to the above-described circuits, but when a measurement starting switch 30 is depressed once, the CPU 29 permits the memory circuits 22 and 26 to receive the data of the video signal Vs only for the measurement time of a vertical scanning interval, operates the signal interval differences in succession, and thereafter delivers a control signal to the data bus control circuits 21, 25, chip select control circuits 23, 27 and address bus control circuits, renders the memory circuits 22 and 26 into the READ mode and interrupts the reception of the data of the video signal, and reads out the content thereof at the timing of $V_{D2}$ of FIG. 9c. The CPU then operates and processes that content and causes a printer 31 to output the content as the data of the subject S.

After a cycle of operation is terminated, the operation of measuring the data from the video signal is resumed. Thereafter, the switch 30 is suitably depressed to effect measurement. FIG. 8a shows a video signal which perceives the horizontal scanning interval, and FIG. 8b shows the output signal 32 of the binarizing comparator 15. FIG. 8c shows a horizontal synchronizing signal $H_D$, and FIG. 8d shows a timing signal 33 comprising a pulse generated at a timing slightly later than the horizontal synchronizing signal $H_D$. FIG. 9a shows a video signal which perceives a vertical scanning interval, FIG. 9b shows a horizontal synchronizing signal $H_D$, FIG. 9c shows a vertical synchronizing signal $V_D$, FIG. 9d shows a signal $V_{D'}$ generated at the timing of the falling of the vertical synchronizing signal $V_{D'}$ and FIGS. 9e–9h show the signals of addresses 1 through 4.

In FIG. 7, reference numeral 16 designates a synchronizing isolation and timing generating circuit, and reference numeral 31 denotes a printer.

The first embodiment of the present invention has been described above, and in the present invention, the angles of incidence of the light beams applied to the left and right sides of the back of the subject need not always be equal to each other and the light beams need not always be applied to positions equidistant from the imaginary spinal line. These can be corrected in the operation process thereafter if they are pre-stored as the amounts of offset. Also, where the interval difference $|x_1| - |x_2|$ in x direction is to be obtained, it is possible to use not the imaginary spinal line but a parallel line spaced apart a predetermined distance from the imaginary spinal line.

The light beam applied to each of the left and right sides of the back of the subject need not always be one but may be plural, e.g., two, and these two light beams may be applied as two parallel slit beams to each of the left and right sides of the back.

The light beams may also be scanning beams which scan in synchronism with the video signal, instead of stationary slit beams.

Further, instead of the video camera 9, an image pickup element such as CCD may be provided and the coordinates $x_1$, $x_2$ may be detected from the output of the CCD and finally, the clinically useful value $\Delta y$ may be calculated.

Figure 10A:
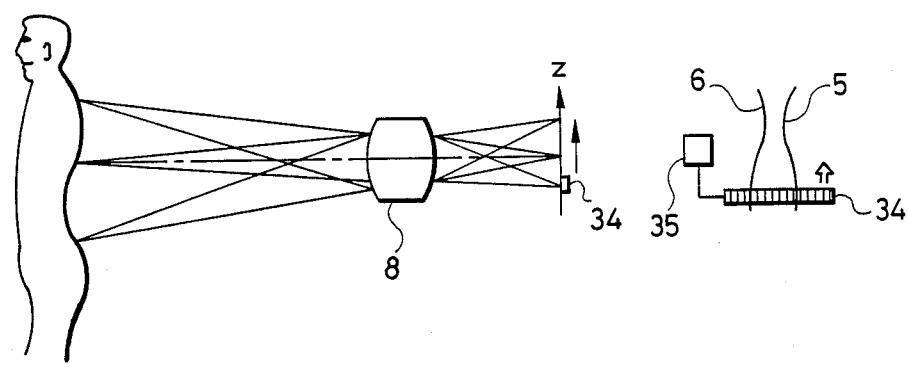
FIGS. 10A and 10B and FIGS. 11A and 11B show embodiments using an image pickup element.
Figure 10B:
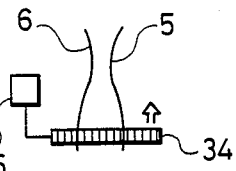

In this case, as shown in FIG. 10A, a CCD 34 on the image plane can be moved in z direction which is the direction of the imaginary spinal line by a motor 35 in a mechanical manner. FIG. 10B is a view as seen from the back.

Figure 11A:
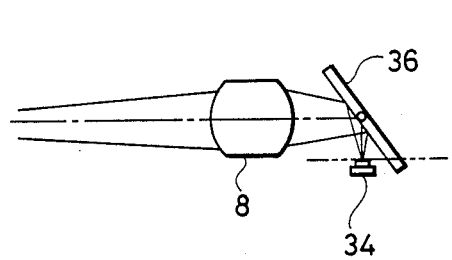
Figure 11B:
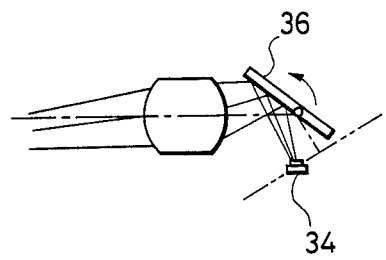

Also, as shown in FIGS. 11A and 11B, a mirror 36 may be provided between the lens 8 and the image plane and, by rotating this mirror, the slit area of the subject body corresponding to the light-receiving area of a one-dimensional CCD may be moved to effect measurement. It is apparent that the CCD may be a two-dimensional element. As the light source, use may be made of a laser, a light-emitting diode or any other light source.

Figure 12A:
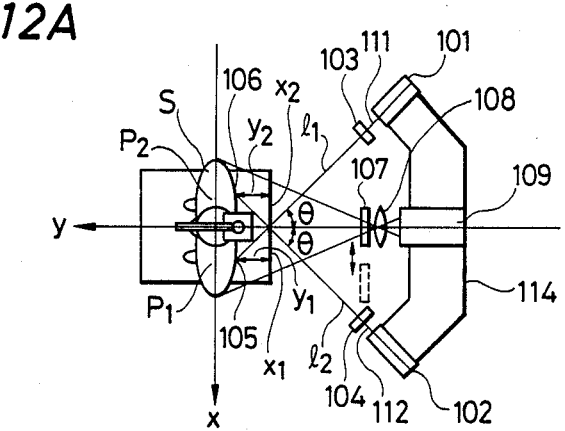
FIGS. 12A and 12B show an embodiment which serves also as a stature measuring apparatus.
Figure 12B:
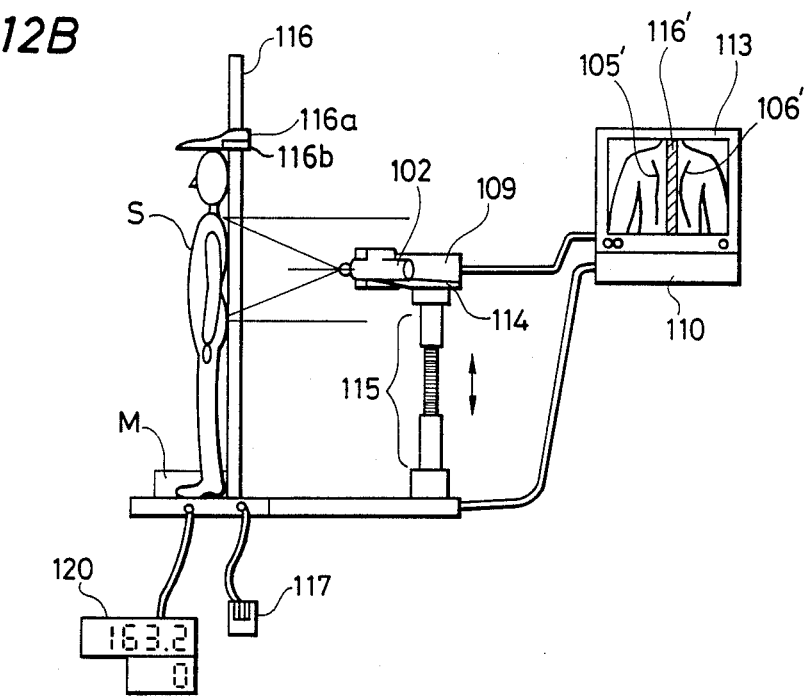

FIG. 12 shows a second embodiment of the present invention which serves also as a stature measuring apparatus. FIG. 12A is a plan view and FIG. 12B is a side view. Reference numeral 116 designates a stature measuring device utilizing a measuring machine using optical or other conventional means. The subject S is caused to stand on a foot type M with his back being stretched along the strut and with a stature measuring slider 116a bearing lightly against the subject's head and when the examiner steps on a foot switch 117, the result of the measurement is immediately output on a display device 120. This information is at the same time transmitted to a signal processor 110, which in turn outputs an instruction to a laser and video camera vertically moving portion 115 so that it is set to a measuring position corresponding to the subject's stature, and immediately thereafter, the moving portion 115 moves to that position and comes to a halt thereat, whereafter measurement of the abnormality of the spinal column is effected. The principle of detection and measurement of the abnormality of the spinal column will be shown below.

As shown in FIG. 12A, at least one light beam is obliquely applied to each of the left and right sides of the back of the subject body along the imaginary spinal line, and the interval difference between the light beam application position and the imaginary spinal line is detected. That is, a beam 111 emitted from a laser 101 is widened in a direction perpendicular to the plane of the drawing sheet by a cylindrical lens 103 whose generatrix direction is in the plane of the drawing sheet, and is applied to the left side of the back of the subject S at an angle of application $\theta$. On the other hand, a beam 112 emitted from a laser 102 is widened in a direction perpendicular to the plane of the drawing sheet by a cylindrical lens 104 whose generatrix direction is in the plane of the drawing sheet, and is applied to the right side of the back of the subject S at an angle of application $\theta$.

Slit beams 105 and 106 applied to the left side and the right side with respect to the spinal column of the subject S are caught by a video camera 109 through a lens 108 and are imaged as 105′ and 106′ on a monitor 113, and the video signals from the video camera 109 are processed by a signal processor 110.

It is known that the uneven state of the back becomes bilaterally asymmetrical if the subject has any abnormality of the spinal column, such as scoliosis, and the present invention uses this information. That is, when, with the point at which a beam $l_1$ emitted from the laser 101 in FIG. 12 and a beam $l_2$ emitted from the laser 102 intersect each other as the reference point, the coordinates of the position $P_1$ at which the beam $l_1$ is applied to the back are $x_1$, $y_1$ and the coordinates of the position $P_2$ at which the beam $l_2$ is applied to the back are $x_2$, $y_2$, the following equations are established:

$$y_1 = -x_1/\tan \theta$$

$$y_2 = x_2/\tan \theta$$

Any abnormality of the spinal column can be judged by detecting the interval difference $|x_1| - |x_2|$ between the light beam application position and the imaginary spinal line along the direction of the imaginary spinal line which is the center line of the subject body, i.e., the direction perpendicular to x direction and y direction, but clinically it is desirable to detect the value of $\Delta y = y_1 - y_2$ along the direction of the imaginary spinal line and judge whether it is within the permissible range.

The imaginary spinal line can be set at the central portion of the strut of the stature measuring device 116 by causing the subject S to stand on the foot type during the measurement of his stature and causing him to assume a correct posture in which his back is stretched so that the uppermost part of his head is in contact with a slider 116a.

Reference numeral 107 designates a filter which transmits therethrough only the wavelength of the applied laser light, and reference numeral 114 denotes a housing.

Figure 13:
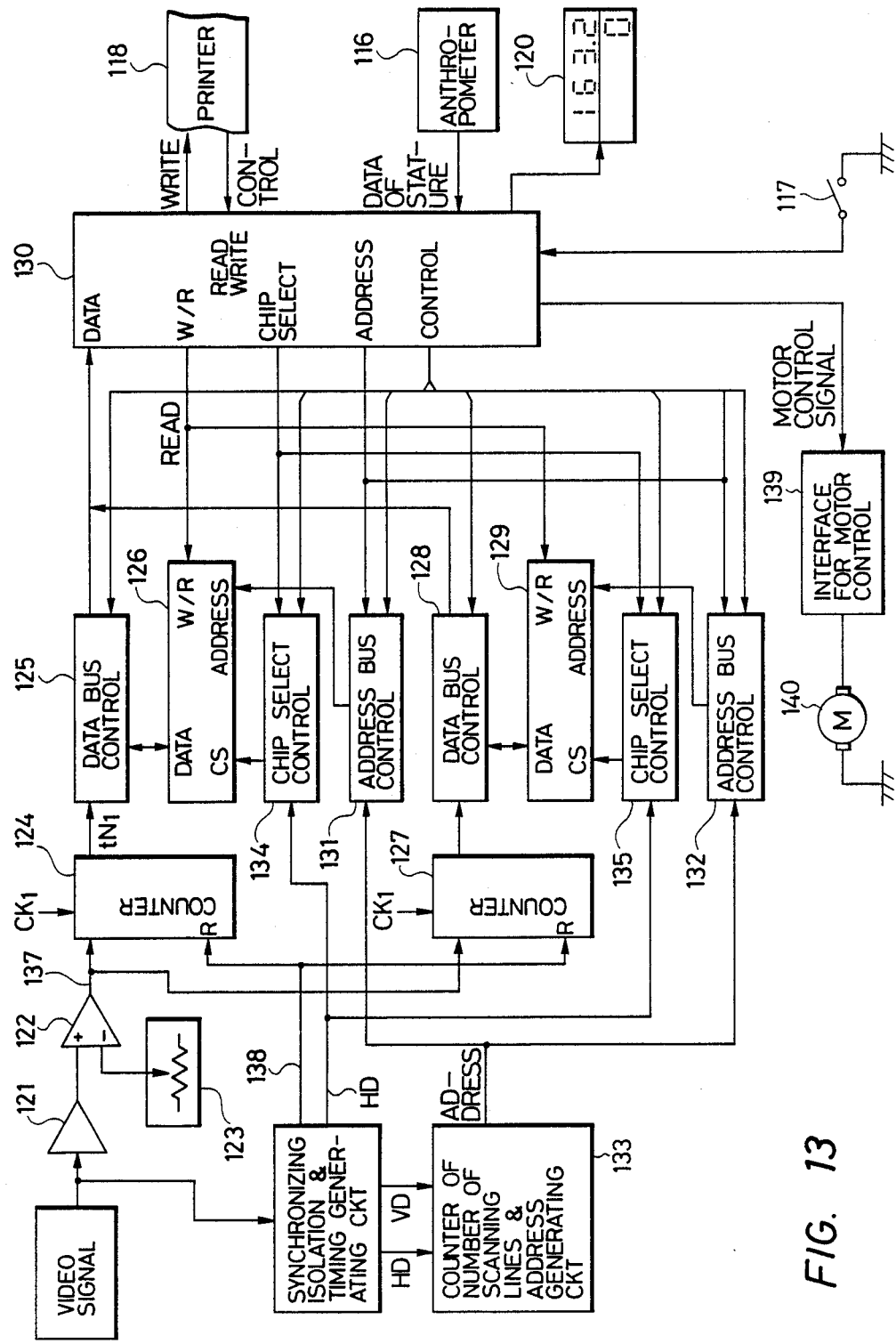
FIG. 13 is a block diagram of the embodiment of FIG. 12.

FIG. 13 shows a block diagram of the apparatus of FIG. 12.

A video signal Vs from a video camera enters an image amplifier 121 and a level higher than the threshold set by a voltage setter 123 is binarized as Hi output by a binarizing comparator 122.

Reference numeral 124 designates a counter for counting the clock number of the time $t_{N1}$ from a horizontal synchronizing signal $H_D$ to the left side beam application position. The output of the counter 124 is input to a data bus control circuit 125. The data bus control circuit 125 functions as a switch for selecting the inputs to a memory 126 and CPU 130.

On the other hand, reference numeral 127 designates a counter for counting the clock number of the time $t_{N2}$ from the horizontal synchronizing signal $H_D$ to the right side beam application position. The output of the counter 127 is input to a data bus control circuit 128.

The two counters 124 and 127 are reset at the timing of the reset 1 of FIG. 8d and count $t_{N1}$ and $t_{N2}$, respectively, and cause memories 126 and 129 to read the contents thereof at $H_{D2}$ through the data bus control circuits 125 and 128. It is to be understood that this operation is effected for each scanning line.

The addresses in the memories give through address bus control circuits 131 and 132 the address signals, as shown in FIG. 9e through 9h which have been produced by a counter of number of scanning lines and address generating circuit 133.

The CPU 130 is normally not related to the above-described circuits, but when a foot switch 117 which is a measurement starting switch is depressed once, the CPU 130 permits the memory circuits 126 and 129 to receive the data of the video signal Vs only for the measurement time of a vertical scanning interval and operates signal interval differences in succession, and thereafter puts out a control signal to the data bus control circuits 125, 128, chip select control circuits 134, 135 and address bus control circuits, renders the memory circuits 126, 129 into the READ mode, interrupts the reception of the data of the video signal and reads out the content thereof at the timing $V_{D2}$ of FIG. 9c. The CPU 130 operates and processes that content and causes a printer 118 to put out the content as the data of the subject S with the data of his stature.

After a cycle of operation is terminated, the operation of measuring the data from the video signal is resumed. Thereafter, the switch 117 is suitably depressed to effect measurement. FIG. 8a shows a video signal which perceives the horizontal scanning interval, and FIG. 8b shows the output signal 137 of the binarizing comparator 122. FIG. 8c shows a horizontal synchronizing signal $H_D$, and FIG. 8d shows a timing signal 138 comprising a pulse generated at a timing slightly later than the horizontal synchronizing signal $H_D$. FIG. 9a shows a video signal which perceives a vertical scanning interval, FIG. 9b shows a horizontal synchronizing signal $H_D$, FIG. 9c shows a vertical synchronizing signal $V_D$, FIG. 9d shows a signal $V_D$, generated at the timing of the falling of the vertical synchronizing signal $V_D$, and FIGS. 9e through 9h show the signals of addresses 1 through 4.

On the other hand, the adjustment of the height during said measurement by the stature is effected in the following manner.

The stature data from a stature measuring device 116 is input to the CPU 130, and as previously described, the CPU is normally not related to the above-described circuits, but when a foot switch 117 is depressed once, the stature data is immediately read into the CPU and by that data, the CPU puts out a motor control signal and the direction revolution and the number of steps of a motor 140 are determined by a motor controlling interface circuit 139, whereby the motor 140 is operated.

The motor becomes reset immediately after the main switch is closed, and the laser and video camera vertically moving portion 115 are set at their predetermined start positions. After the main switch is closed, the moving portion 115 moves during each measurement, but the CPU 130 stores therein the motor control signals in succession and moves the moving portion 115 by an amount corresponding to the difference between the previous data and the next data.

In the present embodiment, the image range in the direction of the imaginary spinal line can also be varied in accordance with the stature.

That is, it is also possible to cause only the detected range to be displayed from the image in the video camera, electrically eliminate the non-detected range and cause only the detected range to shine on the monitor, whereby mixing of noise is eliminated during measurement.

Also, the length in the direction of slit of the slit beams applied to the back of the subject can be varied in accordance with the stature. This can be accomplished by replacing the cylindrical lenses 103 and 104 with cylindrical lenses of different refractive powers or by optically providing a zoom lens in the optical path.

The slider 116a adapted to contact the head of the subject may be provided with a switch 116b correspondingly to the measurement of the stature and this switch may be endowed with the function of initiating the detection of abnormality of the spinal column.

In the video signal processing of the standard scanning, the speed is high and therefore, the interface to a microcomputer has heretofore been cumbersome, but the interface will become easy if a method of first writing the data into a memory by hardware as in the embodiment of FIG. 7 and causing the microcomputer to process the result is adopted.

We claim:

1. An apparatus for detecting abnormality of a subject's spinal column, comprising:
   irradiation means for applying at least one light beam, to each of a left back side and a right back side of the subject, at an oblique angle in a plane normal to a reference line extending down a center of the back of the subject;
   position detecting means having a detecting surface for detecting an irradiated position on each side of the back to which the light beam is applied in said plane; and
   position changing means for changing the position of said detecting surface along the direction of the reference line; and means for detecting an abnormality of the spinal column on the basis of relative variations of said irradiated positions on each side of the back as detected by said position detecting means and for producing an output indicative of a condition of the subject's spinal column.

2. An apparatus according to claim 1, wherein said at least one light beam is a slit beam extending parallel to the reference line.

3. An apparatus according to claim 1, wherein said at least one light beam is a scanning beam scanned in a direction parallel to the reference line.

4. An apparatus according to claim 1, further comprising a wavelength selecting filter, interposed in an optical path between said position detecting means and the reference lines for transmitting only said at least one light beam to said position detecting means so as to prevent any other beam, except said at least one light beam, from entering said position detecting means.

5. An apparatus according to claim 1 wherein said irradiation means is disposed in a position such that the oblique angle of the light beam irradiated onto the right back side of the subject is identical to the oblique angle of the light beam irradiated onto the left back side of the subject.

6. An apparatus according to claim 1, wherein said irradiation means is disposed in a position such that an irradiated point on the right back side of the subject and an irradiated point on the left back side of the subject are equidistant from the reference line.

7. An apparatus according to claim 1, wherein said position detecting means is a video camera means for generating a video signal.

8. An apparatus according to claim 1, wherein said position detecting means is an image pick-up element.

9. An apparatus according to claim 8, wherein said image pick-up element is a one-dimensional image pick-up element disposed substantially normal to the first plane.

10. An apparatus according to claim 9, wherein said position changing means moves said one-dimensional image pick-up element in the direction in which the reference line extends.

11. An apparatus according to claim 9, wherein said position changing means includes an optical path deflector rotatable about an axis perpendicular to the reference line and disposed in an optical path of a light beam between said one-dimensional image pick-up element and a lens of said position detecting means.

12. An apparatus according to claim 11, wherein said optical path deflecting means is a rotatable mirror.

13. An apparatus for detecting abnormality of a subject's spinal column, in which its height may be changed in accordance with a stature of the subject, comprising:
   irradiation means for applying at least one light beam to each of a left back side and a right back side of the subject, at an oblique angle in a plane normal to a reference line extending down a center of the back of the subject;
   means for detecting the stature of the subject;
   means for adjusting the height of said irradiation means responsive to said means for detecting;
   position detecting means having a detecting surface for detecting an irradiated position on each side of the back to which the light beam is applied in said plane; and
   position changing means for changing the position of said detecting surface in the direction of the reference line; and means for detecting an abnormality of spinal column on the basis of relative variations of said irradiated positions on each side of the back as detected by said position detecting means and for producing an output indicative of a condition of the subject's spinal column.

14. An apparatus according to claim 13, wherein said at least one light beam is a slit beam extending parallel to the reference line.

15. An apparatus according to claim 14, wherein said irradiation means comprises means for varying the longitudinal length of the slit beam in accordance with the stature of the subject.

16. An apparatus according to claim 13, wherein said at least one light beam is a scanning beam scanned along a direction in parallel to the reference line.

17. An apparatus according to claim 13, wherein said position detecting means is a video camera generating a video signal.

18. An apparatus according to claim 13, further comprising a wavelength selecting filter means, interposed in an optical path between said position detecting means and the reference line for transmitting only said at least one light beam to said position detecting means so as to prevent any other beam except said at least one light beam applied to the back of the subject from entering said position detecting means.

19. An apparatus according to claim 13, further comprising a slider movable in accordance with the stature of the subject, and a switch actuated by said slider when in contact with the top of a head of the subject to start operation of spinal column abnormality detection.

20. An apparatus according to claim 13, further comprising a slider movable in accordance with the stature of the subject, in which the stature of the subject may be measured on the basis of a position where the slider contacts the head of the subject.

* * * * *

UNITED STATES PATENT AND TRADEMARK OFFICE
CERTIFICATE OF CORRECTION

PATENT NO. : 4,832,049
DATED : May 23, 1989
INVENTOR(S) : MACHIKO MATSUSHITA ET AL.

It is certified that error appears in the above-identified patent and that said Letters Patent is hereby corrected as shown below:

COLUMN 3

Line 43, "from" should read --are from--.

COLUMN 8

Line 1, "reference lines" should read --reference line,--.
Line 37, "optical path deflecting means" should read --optical path deflector--.
Line 56, "of spinal column" should read --of the spinal column--.

COLUMN 9

Line 3, "in" should be deleted.
Line 10, "reference line" should read --reference line,--.

Signed and Sealed this

Twenty-seventh Day of March, 1990

Attest:

JEFFREY M. SAMUELS

*Attesting Officer*   *Acting Commissioner of Patents and Trademarks*